(12) United States Patent
Ehr et al.

(10) Patent No.: US 9,034,353 B2
(45) Date of Patent: May 19, 2015

(54) MESO-SIZED CAPSULES USEFUL FOR THE DELIVERY OF AGRICULTURAL CHEMICALS

(75) Inventors: Robert J. Ehr, Indianapolis, IN (US); Thomas H. Kalantar, Midland, MI (US); Lei Liu, Carmel, IN (US); Dale C. Schmidt, Midland, MI (US); Mike P. Tolley, Indianapolis, IN (US); Kerrm Y. Yau, Carmel, IN (US); Qiang Zhang, Fayetteville, AR (US); Min Zhao, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 232 days.

(21) Appl. No.: 12/850,676

(22) Filed: Aug. 5, 2010

(65) Prior Publication Data

US 2011/0045975 A1    Feb. 24, 2011

Related U.S. Application Data

(60) Provisional application No. 61/232,044, filed on Aug. 7, 2009.

(51) Int. Cl.
| | | |
|---|---|---|
| *A01N 25/34* | (2006.01) | |
| *A01N 25/32* | (2006.01) | |
| *A01N 43/72* | (2006.01) | |
| *A01N 25/28* | (2006.01) | |

(52) U.S. Cl.
CPC ...................................... *A01N 25/28* (2013.01)

(58) Field of Classification Search
USPC ........................... 424/408; 504/105, 223, 359
See application file for complete search history.

(56) References Cited

U.S. PATENT DOCUMENTS

| | | | |
|---|---|---|---|
| 4,285,750 A | 8/1981 | DeMartino | |
| 4,757,105 A | 7/1988 | Kopp | |
| 5,225,118 A | 7/1993 | Juang et al. | |
| 6,540,808 B2 * | 4/2003 | Ma et al. | 71/27 |
| 7,241,804 B1 | 7/2007 | Hockenberry et al. | |
| 2003/0059473 A1 | 3/2003 | Montasser et al. | |
| 2003/0138500 A1 | 7/2003 | Parker et al. | |
| 2004/0091546 A1 * | 5/2004 | Johnson et al. | 424/501 |
| 2005/0271735 A1 * | 12/2005 | Stover et al. | 424/490 |
| 2006/0281834 A1 * | 12/2006 | Lee et al. | 523/201 |
| 2007/0020304 A1 * | 1/2007 | Tamarkin et al. | 424/405 |
| 2007/0196413 A1 | 8/2007 | Stern et al. | |
| 2008/0207445 A1 | 8/2008 | Dexter | |
| 2009/0238878 A1 | 9/2009 | Singh | |
| 2010/0261606 A1 | 10/2010 | Patel et al. | |
| 2012/0035054 A1 * | 2/2012 | Ehr et al. | 504/227 |

FOREIGN PATENT DOCUMENTS

| | | |
|---|---|---|
| JP | 07-053835 | 2/1995 |
| JP | 2003-144904 | 5/2003 |
| WO | WO01/94001 | 12/2001 |
| WO | WO 02/087343 | 11/2002 |
| WO | WO 03/101606 A1 | 12/2003 |
| WO | WO 2005/002719 | 1/2005 |
| WO | WO 2009/153231 | 12/2009 |

OTHER PUBLICATIONS

Gonzalez-Melendi et al., Annals of Botany, 2008, 1010, 187-195. Available online on Nov. 12, 2007.*
Boehm et al., J. Microencapsulation, 2000, 17(2), 195-205.*
Montasser et al., International Journal of Pharmaceutics, 2007, 335, 176-179.*
Liu et al., Pest Manag Sci, 2008, 64, 808-812.*
Gonzalez-Melendi, P., et al., "Nanoparticles as smart treatment-delivery systems in plants: Assessment of different techniques of microscopy for their visualization in plant tissues," Annals of Botany, Academic Press, London, GB, vol. 101, No. 1, Jan. 1, 2008, pp. 187-195.
Corredor, Eduardo, et al., "Nanoparticle penetration and transport in living pumpkin plants: in situ subcellular identification," BMC Plant Biology, Biomed Central, London, GB, vol. 9, No. 1, Apr. 23, 2009, p. 45.
International Searching Authority, International Search Report for PCT/US2010/044484, mailing date Aug. 31, 2011, 4 pages.
International Searching Authority, Written Opinion for PCT/US2010/044484, mailing date Aug. 31, 2011, 5 pages.
International Searching Authority, International Preliminary Report on Patentability for PCT/US2010/044484, mailing date Feb. 7, 2012, 6 pages.

* cited by examiner

*Primary Examiner* — Abigail Fisher
(74) *Attorney, Agent, or Firm* — C.W. Arnett; Faegre Baker Daniels LLP

(57) ABSTRACT

Disclosed herein are mesocapsules that include agriculturally active ingredients. These mesocapsules are comprised of a polyurea shell and include hydrophilic groups on their surfaces and have a volume-average diameter of about 500 nm or less and some of them have a volume-average diameter on the order of about 300 nm or less. These mesocapsules are suited for delivering active ingredients that are not very soluble in water. Methods for making these mesocapsules include interfacial polycondensation reactions carried out in the presence of surfactants and other methods in which all or most of the surfactant is replaced by adding amino acids to the aqueous phase of the interfacial reaction mixture before forming the final emulsion.

24 Claims, 7 Drawing Sheets

FIGURE 1

|  | 20% Glycine-Na | 20% Glycine-K | 25% L-lysine | 37.5% L-lysine-Na | 37.5% L-lysine-K |
|---|---|---|---|---|---|
| Glycine | 12.8 g | 12.0 g | - | - | - |
| L-Lysine | - | - | 25 g | 6.00 g | 6.00 g |
| 5 N Sodium Hydroxide in Water | 33.9 g | - | - | 8.20 g | - |
| 45 wt.% Potassium Hydroxide in Water | - | 16.6 g | - | - | 5.13 g |
| Water | 17.3 g | 31.4 g | 75 g | 1.80 g | 4.89 g |

FIGURE 2

|  | Sample Designation | | | | |
|---|---|---|---|---|---|
|  | 1 | 2 | 3 | 4 | 5 |
| *Combine in Oil Phase* | | | | | |
| Fenbuconazole | 0.22 g | 0.22 g | 0.22 g | 0.22 g | 0.70 g |
| Benzyl Acetate | 2.85 g | 2.47 g | 2.85 g | 2.83 g | 6.75 g |
| Hexadecane | 0.15 g | 0.13 g | 0.15 g | 0.15 g | 0.36 g |
| PAPI™ 27 polymeric MDI[1] | 0.80 g | 1.21 g | 0.81 g | 0.82 g | 4.22 g |
| *Surfactant Addition* | | | | | |
| Sodium Dodecyl Sulfate | 0.12 g | 0.06 g | 0.020 | 0.12 g | 0.36 g |
| *Combine in Aqueous Phase* | | | | | |
| Water | 36.1 g | 35.8 g | 35.8 g | 36.0 g | 28.1 g |
| *Glycine Addition* | | | | | |
| 20% Glycine-Na | - | 0.10 g | 0.22 g | - | - |
| 20% Glycine-K | - | 0.10 g | - | - | - |
| *Crosslinker Addition* | | | | | |
| 25% L-lysine | - | - | - | - | 8.25 g |
| 37.5% L-lysine-Na | - | 0.37 g | 0.94 g | - | - |
| 37.5% L-lysine-K | 1.06 g | 0.37 g | - | - | - |
|  | | | | | |
| Particle Volume Average Diameter | 86 nm | 98 nm | 107 nm | 105 nm | 144 nm |

[1] PAPI™ 27 (The Dow Chemical Company)

FIGURE 3

The table specifies components levels for each formulation.

| | | Sample Designation | | | | | |
|---|---|---|---|---|---|---|---|
| | | 10 | 11 | 8 | 6 | 14 | 12 |
| Component | Ingredient[1] | Wt % | Wt % | Wt % | Wt % | Wt % | Wt % |
| Herbicide AI | Atrazine | 1.19 | | | | | |
| Herbicide AI | Fluroxypyr-Meptyl | | 5.73 | | | | |
| Fungicide AI | Epoxiconazole | | | 1.40 | | | |
| Fungicide AI | 328255-92-1 | | | | 1.80 | | |
| Insecticide AI | Spinosad | | | | | 2.81 | |
| Insecticide AI | Indoxacarb | | | | | | 2.13 |
| Solvent | cyclohexanone | 17.37 | | | 15.79 | 7.82 | |
| Solvent | Aromatic 200 | 6.20 | 13.69 | 6.01 | 6.77 | 7.81 | |
| Solvent | acetophenone | | | 17.30 | | | |
| Solvent | benzyl acetate | | | | | | 18.22 |
| Monomer 1 | PAPI™ 27 | 6.45 | 5.08 | 6.45 | 6.45 | 4.87 | 5.33 |
| Monomer 2 | L-lysine | 3.52 | 2.77 | 3.52 | 3.52 | 2.66 | 2.61 |
| Ultrahydrophobe | Indopol™ H15 | 0.97 | 0.76 | 0.97 | 0.97 | 0.73 | |
| Ultrahydrophobe | hexadecane | | | | | | 0.95 |
| Dispersant | Sodium Lauryl Sulfate | 0.97 | 0.76 | 0.97 | 0.97 | 0.73 | 0.80 |
| Biocide | Proxel™ GXL | 0.10 | 0.10 | 0.10 | 0.10 | 0.10 | |
| Water Balance | Water | 63.19 | 70.96 | 63.19 | 63.19 | 72.14 | 70.0 |
| | total | 100.00 | 100.00 | 100.00 | 100.00 | 100.00 | 100.00 |
| Particle Volume Average Diameter | | 285 nm | 306 nm | 250 nm | 344 nm | 286 nm | 123 nm |

[1] PAPI™ 27 (The Dow Chemical Company); Indopol™ H15 (INEOS Oligomers); Proxel™ GXL (Arch UK Biocides, Ltd.).

FIGURE 4

| Sample Number | Active Ingredient | AI type | Formulation | Weight % active |
|---|---|---|---|---|
| 1 | Fenbuconazole | Fungicide | Polyurea mesocapsule | 0.53 |
| 2 | Fenbuconazole | Fungicide | Polyurea mesocapsule | 0.46 |
| 3 | Fenbuconazole | Fungicide | Polyurea mesocapsule | 0.54 |
| 4 | Fenbuconazole | Fungicide | Polyurea mesocapsule | 0.43 |
| 5 | Fenbuconazole | Fungicide | Polyurea mesocapsule | 0.99 |
| Indar 75WP | Fenbuconazole | Fungicide | Wettable powder | 75 |
| 6 | 328255-92-1 | Fungicide | Polyurea mesocapsule | 2.26 |
| 7 | 328255-92-1 | Fungicide | Suspension concentrate | 8 |
| 8 | Epoxiconazole | Fungicide | Polyurea mesocapsule | 1.4 |
| 9 | Epoxiconazole | Fungicide | Suspension concentrate | 10 |
| 10 | Atrazine | Herbicide | Polyurea mesocapsule | 1.19 |
| Aatrex Nine-0 | Atrazine | Herbicide | Water dispersible granule | 90 |
| 11 | Fluroxypyr-meptyl | Herbicide | Polyurea mesocapsule | 5.73 |
| Casino 25 WP | Fluroxypyr-meptyl | Herbicide | Wettable powder | 25 |
| 12 | Indoxacarb | Insecticide | Polyurea mesocapsule | 2.13 |
| 13 | Indoxacarb | Insecticide | Suspension concentrate | 10 |

AAtrex Nine-0™ (Syngenta); Indar™ 75WP and Casino™ 25WP (Dow AgroSciences, LLC).

FIGURE 5

| Rate (g ai/ha) | Percent Disease in Curative Test 21 Days after Application | | | | | |
|---|---|---|---|---|---|---|
| | Sample | | | | | |
| | 1 | 2 | 3 | 4 | 5 | Indar |
| 62.5 | 0 | 18 | 2 | 0 | 25 | 42 |
| 20.8 | 7 | 48 | 10 | 60 | 27 | 67 |
| 6.9 | 40 | 73 | 14 | 55 | 63 | 75 |
| 2.3 | 38 | 75 | 42 | 60 | 73 | 62 |
| 0.77 | 80 | 75 | 75 | 87 | 60 | 90 |

FIGURE 6

| Rate (g ai/ha) | Percent Disease in Protectant Test 21 Days after Application | | | | | |
|---|---|---|---|---|---|---|
| | Sample | | | | | |
| | 1 | 2 | 3 | 4 | 5 | Indar |
| 62.5 | 0 | 0 | 0 | 0 | 0 | 0 |
| 20.8 | 0 | 0 | 0 | 0 | 0 | 1 |
| 6.9 | 0 | 0 | 0 | 3 | 0 | 2 |
| 2.3 | 6 | 7 | 1 | 2 | 11 | 3 |
| 0.77 | 48 | 13 | 11 | 28 | 52 | 47 |

FIGURE 7

| Sample Number | Active ingredient | Formulation | Percent Disease |
|---|---|---|---|
| 6 | 328255-92-1 | Meso capsule | 33.5 |
| 7 | 328255-92-1 | Suspension concentrate | 45.5 |
| 8 | Epoxiconazole | Meso capsule | 21.9 |
| 9 | Epoxiconazole | Suspension concentrate | 27 |

FIGURE 8

| Sample | Rate (g ai/Ha) | ABUTH | CASOB | SETFA | DIGSA | SIDSP | Average |
|---|---|---|---|---|---|---|---|
| AAtrex Nine-0 | 280 | 31.7 | 5 | 0 | 0 | 10 | 9.3 |
| AAtrex Nine-0 | 560 | 33.3 | 7.3 | 2 | 0 | 15 | 11.5 |
| AAtrex Nine-0 | 1120 | 36.7 | 10 | 4 | 0 | 18.3 | 13.8 |
| AAtrex Nine-0 | 2240 | 46.7 | 46.7 | 4 | 6.7 | 26.7 | 26.2 |
| 10 | 280 | 30 | 35 | 4 | 0 | 10 | 15.8 |
| 10 | 560 | 61.7 | 75 | 18.3 | 10 | 16.7 | 36.3 |
| 10 | 1120 | 60 | 86.7 | 38.3 | 23.3 | 38.3 | 49.3 |
| 10 | 2240 | 78.3 | 95.3 | 61.7 | 46.7 | 66.7 | 69.7 |
| Control |  | 0 | 0 | 0 | 0 | 0 | 0 |

FIGURE 9

| Sample | Rate (g ae/ha) | KCHSC | STEME | POLCO | CHEAL | SIDSP | CASOB | ABUTH | AMBEL | Average |
|---|---|---|---|---|---|---|---|---|---|---|
| CASINO 25WG | 12.5 | 30.0 | 21.0 | 9.0 | 0.0 | 21.7 | 0.0 | 8.0 | 6.0 | 12.0 |
| CASINO 25WG | 25 | 50.0 | 41.0 | 20.0 | 0.0 | 25.0 | 1.0 | 27.5 | 5.0 | 21.2 |
| CASINO 25WG | 50 | 61.0 | 36.0 | 53.0 | 0.0 | 31.7 | 0.0 | 37.5 | 23.3 | 30.3 |
| CASINO 25WG | 100 | 66.0 | 52.0 | 54.0 | 0.0 | 43.3 | 0.7 | 55.0 | 55.0 | 40.8 |
| CASINO 25WG | 200 | 75.0 | 70.0 | 60.0 | 2.0 | 57.0 | 5.0 | 60.0 | 71.7 | 50.1 |
| 11 | 12.5 | 55.0 | 50.0 | 49.0 | 0.0 | 27.0 | 0.0 | 20.0 | 23.3 | 28.0 |
| 11 | 25 | 64.0 | 64.0 | 62.0 | 0.0 | 39.3 | 0.7 | 37.5 | 43.3 | 38.8 |
| 11 | 50 | 66.0 | 80.0 | 62.0 | 0.7 | 56.7 | 2.7 | 66.0 | 58.3 | 49.0 |
| 11 | 100 | 80.0 | 65.0 | 76.0 | 0.0 | 63.3 | 8.0 | 72.0 | 77.7 | 55.2 |
| 11 | 200 | 87.0 | 88.0 | 69.0 | 10.3 | 75.0 | 8.0 | 85.0 | 78.7 | 62.6 |
| UNTREATED |  | 0.0 | 0.0 | 0.0 | 0.0 | 0.0 | 0.0 | 0.0 | 0.0 | 0.0 |

FIGURE 10

| Sample | Rate ppm | Days Post-Treatment | Mean % Leaf Disk Consumption |
|---|---|---|---|
| 12 | 2.5 | 3 | 21.25 |
| 13 | 2.5 | 3 | 75.62 |
| Untreated | 0 | 3 | 56.25 |
| 12 | 2.5 | 4 | 45 |
| 13 | 2.5 | 4 | 96.5 |
| Untreated | 0 | 4 | 92 |
| 12 | 10 | 3 | 5.5 |
| 13 | 10 | 3 | 29 |
| Untreated | 0 | 3 | 45 |
| 12 | 10 | 4 | 15.25 |
| 13 | 10 | 4 | 40.25 |
| Untreated | 0 | 4 | 79.13 |

FIGURE 11

| Sample | Rate ppm | Days Post-Treatment | % Corrected Mortality |
|---|---|---|---|
| 12 | 10 | 4 | 66.67 |
| 13 | 10 | 4 | 47.62 |
| Untreated | 0 | 4 | 0 |

FIGURE 12

| | | % Mortality at indicated day after treatment | | | | | | |
|---|---|---|---|---|---|---|---|---|
| Sample | Rate % | Day 1 | Day 2 | Day 3 | Day 4 | Day 5 | Day 6 | Day 7 |
| 12 | 0.01 | 50% | 70% | 70% | 70% | 70% | 80% | 80% |
| 13 | 0.01 | 50% | 50% | 50% | 50% | 50% | 50% | 60% |
| Untreated | 0 | 0% | 0% | 0% | 0% | 0% | 0% | 0% |

FIGURE 13

| Sample | Rate % | % Mortality at indicated day after treatment | | | | | | |
|---|---|---|---|---|---|---|---|---|
| | | Day 1 | Day 2 | Day 3 | Day 4 | Day 5 | Day 6 | Day 7 |
| 12 | 0.1 | 40% | 80% | 90% | 90% | 90% | 90% | 90% |
| 13 | 0.1 | 0% | 40% | 60% | 60% | 70% | 70% | 70% |
| Untreated | 0 | 0% | 0% | 0% | 0% | 0% | 0% | 0% |

FIGURE 14

| Sample | Rate % | Day 1 mg Consumed | Day 2 mg Consumed | Day 3 mg Consumed |
|---|---|---|---|---|
| 12 Encapsulated bait | 0.1 | 22.3 | 0.1 | 1.7 |
| 13 bait | 0.1 | 108.3 | 0 | 0 |
| Untreated water bait | 0 | 126.4 | 27.9 | 32.2 |

MESO-SIZED CAPSULES USEFUL FOR THE DELIVERY OF AGRICULTURAL CHEMICALS

CROSS-REFERENCE TO RELATED APPLICATIONS

This Application claims the benefit of U.S. Provisional Application 61/232,044 filed on Aug. 7, 2009, which is expressly incorporated by reference herein.

FIELD OF THE INVENTION

Various aspects relate to materials and methods for making meso-sized capsules and using them to deliver active ingredients such as fungicides, insecticides, miticides, herbicides, safeners and modifiers of plant physiology or structure to plants.

BACKGROUND

Modern agricultural pesticide active ingredients including fungicides, insecticides miticides, herbicides and safeners as well as modifiers of plant physiology and structures and nutrients are typically formulated as liquid or solid formulations. These formulations are designed so that they are convenient for the grower or end user to use and so that the inherent biological activity of the active ingredient is properly expressed. The purpose of various aspects and embodiments disclosed herein is to further improve the effectiveness and efficiency of the delivery and biological activity of active ingredients used in agriculture and general pest management.

DEFINITIONS

The term "agricultural active ingredient (AI)" as used herein refers to a chemical used in agriculture, horticulture and pest management for protection of crops, plants, structures, humans and animals against unwanted organisms such as fungal and bacterial plant pathogens, weeds, insects, mites, algae, nematodes and the like. Specifically, active ingredients used for these purposes include fungicides, bactericides, herbicides, insecticides, miticides, algaecides, nemtocides and fumigants. The term "agricultural active ingredient" also includes insect attractants, repellants and pheromones, modifiers of plant physiology or structure and herbicide safeners.

The term "meso" as used herein describes particles, capsules, or droplets which have a volume-average diameter of between about 30 nm and about 500 nm. The term "mesocapsule" as used herein describes capsules or core-shell particles having a volume-average diameter of between about 30 nm and about 500 nm.

The term "about" means a range of plus to minus 10 percent, e.g. about 1 included values from 0.9 to 1.1.

The term "poorly water soluble" as used herein means active ingredients with solubility in water of less than about 1000 ppm. Preferably, the poorly water soluble active ingredient has a solubility in water of less than 100 ppm, more preferably less than 10 ppm.

The term "water immiscible solvent" as used herein means a solvent or mixture of solvents with a solubility in water of about 10 g/100 ml or less.

The term "essentially no surfactant" as used herein means a surfactant concentration of less than 1 weight percent with respect to the oil phase and more preferably less than 0.5 weight percent of a surfactant with respect to the oil phase.

The term "surfactant" as used herein means a substance used to create and/or stabilize an emulsion. Surfactants include nonionic, anionic, cationic, or combinations of nonionic and anionic or nonionic and cationic. Examples of suitable surfactants include alkali metal lauryl sulfates such as sodium dodecyl sulfate, alkali metal fatty acids salts such as sodium oleate and sodium stearate, alkali metal alkylbenzene sulfonates such as sodium dodecylbenzene sulfonate, polyoxyethylene nonionics, and quaternary ammonium surfactants. Standard reference sources from which one of skill in the art can select suitable surfactants, without limitation to the above mentioned classes, include Handbook of Industrial Surfactants, Fourth Edition (2005) published by Synapse Information Resources Inc, and McCutcheon's Emulsifiers and Detergents, North American and International Editions (2008) published by MC Publishing Company.

The term "interfacial condensation" as used herein means a reaction between two complimentary, organic intermediates that takes place at an interface between two immiscible liquids in which one immiscible liquid is dispersed in the other immiscible liquid. An example of an interfacial condensation reaction is given by U.S. Pat. No. 3,577,515 which is expressly incorporated by reference herein. A "core-shell" capsule is a capsule created by an interfacial condensation reaction that takes place between two immiscible phases, in which the first immiscible phase is a dispersed phase, the second immiscible phase is a continuous phase; and the dispersed phase or core is encapsulated within a shell formed by the reaction of two complimentary, organic intermediates which form the shell and the core-shell capsule is dispersed within the continuous phase.

The term "crosslinker" as used herein means a substance that initiates and facilitates reaction of polymer precursors to form a core shell particle. The crosslinker becomes part of the polymer structure comprising the core shell particle. Examples of crosslinkers as used herein include water, water-soluble diamines, water soluble polyamines, water soluble polyamino acids, water soluble diols, water soluble polyols, and mixtures thereof.

SUMMARY

One embodiment of the present disclosure includes a composition for the delivery of an agricultural active ingredient, comprising a mesocapsule, the mesocapsule having a polymer shell, and a poorly water soluble agricultural active ingredient, wherein the active ingredient is at least partially included within the polymer shell, the mesocapsules having a volume-average particle diameter between about 30 nm and about 500 nm.

Another embodiment of the present disclosure includes a method for synthesizing a mesocapsule, comprising the steps of providing an oil phase, the oil phase including at least one agricultural active ingredient and one or more polymer precursors capable of reacting to form a shell, supplying an aqueous phase, the aqueous phase including water and at least one crosslinker, adding a surfactant to at least one of the aqueous phase and the oil phase, mixing the oil and the aqueous phases under shear conditions sufficient to form an emulsion having meso-sized droplets with a volume-average diameter of about 500 nm or less, and reacting the polymer precurser with the crosslinker to form the mesocapsule.

Another embodiment of the present disclosure includes a method for synthesizing a surfactant free mesocapsule, comprising the steps of providing an oil phase, the oil phase including at least one agricultural active ingredient and at least one polyisocyanate, supplying an aqueous phase, wherein the aqueous phase includes at least one component wherein the component includes at least one functional moiety that is either a primary or secondary amine or a primary or secondary amino group and additionally at least one hydrophilic functional group, mixing the oil and the aqueous phases to form an emulsion, and reacting polyisocyanate with a crosslinker to form the mesocapsule.

BRIEF DESCRIPTION OF THE FIGURES

FIG. 1 summarizes the components of stock solutions of glycine and lysine that were prepared and used to synthesize the exemplary meso-sized capsules disclosed herein.

FIG. 2 summarizes the ingredients that were combined in order to synthesize the exemplary mesocapsules of fenbuconazole disclosed herein.

FIG. 3 summarizes the ingredients that were combined in order to synthesize exemplary mesocapsules of herbicides, fungicides and insecticides disclosed herein.

FIG. 4 includes a list of exemplary formulations tested for their effectiveness as pesticides; the table lists the formulations and provides an estimate of the wt. % of agricultural active ingredient (AI) in each formulation.

FIG. 5 summarizes the results of testing various formulations identified in FIG. 4 for their ability to cure fungal infections caused by *Septoria tritici* on plants.

FIG. 6 summarizes the results of testing various formulations identified in FIG. 4 for their ability to prevent fungal infections caused by *Septoria tritici* in plants.

FIG. 7 summarizes the results of testing various formulations identified in FIG. 4 for their ability to prevent fungal infections caused by *Puccinia recondita* f sp. *tritici* in plants.

FIG. 8 summarizes the results of testing various atrazine formulations identified in FIG. 4 for their ability to control weeds. Data are percent weed control.

FIG. 9 summarizes the results of testing various fluoroxypyr-meptyl formulations identified in FIG. 4 for their ability to control weeds. Data are percent weed control.

FIG. 10 summarizes the results of testing various indoxacarb formulations identified in FIG. 4 for their ability to reduce leaf feeding by Diamondback moth.

FIG. 11 summarizes the results of testing various indoxacarb formulations identified in FIG. 4 for their ability to cause Diamondback moth mortality.

FIG. 12 summarizes the results of testing various indoxacarb formulations identified in FIG. 4 for their ability to cause German cockroach mortality when administered by injection.

FIG. 13 summarizes the results of testing various indoxacarb formulations identified in FIG. 4 for their ability to cause German cockroach mortality when administered by topical application.

FIG. 14 summarizes the results of testing various indoxacarb formulations identified in FIG. 4 for their ability to cause feeding cessation by German cockroach when administered by bait ingestion.

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

Discovering, developing and producing effective and economical agricultural active ingredients (AIs) such as fungicides, insecticides, herbicides, safeners, modifiers of plant physiology or structure, and the like is only part of the challenge facing the agriculture chemical industry. It is also important to develop effective formulations of these types of compounds to enable their efficient and economical application. Cost considerations alone dictate an ever-growing need for new formulations and methods for making and using AIs. This need is especially acute when the effectiveness of AIs is limited or when they are difficult to handle and apply effectively as desired due to problems such as low solubility in aqueous solutions or poor bioavailability in and on plants and insects.

As used herein, the terms 'plant' and 'agricultural crop' shall mean any commercially propagated plant whether produced by conventional plant breeding, vegetative propagation or by employing techniques of genetic modification.

One of the most effective ways of improving the efficacy of AIs is to increase the penetration of the AIs' into the plant either through the root system or through the stem and leaf surfaces or into an insect through the gut or exoskeleton. Often times this involves formulating the AIs in a water soluble form. However, many otherwise effective AIs are not very soluble in water. Accordingly, a compound or formulation that increases the penetration of poorly water soluble AIs into and through plants and insects has the potential to improve overall effectiveness of a wide variety of AIs including, for example, AIs that are not very soluble in water.

Some aspects and embodiments disclosed herein increase an agricultural active ingredient's bioavailability by encapsulating the AI into a polyurea core-shell particle of very small size e.g., a mesocapsule having a volume-average particle diameter of about 500 nm or less; in some embodiments the mesocapsules diameter is on the order of 300 nm or less. Some of these mesocapsules include a surface functionalized with biologically compatible hydrophilic functional groups such as carboxylic acid groups. In many applications AIs at least partially encapsulated in mesocapsules more effectively penetrate plants and insects and are more efficiently transported within the plant and through the plant than are AI's that are not encapsulated.

In addition to their utility for formulating and delivering pesticidal active ingredients, many of the mesocapsules and methods for making meso-sized encapsulated formulations disclosed herein have utility when used in combination with other active ingredients such as biocides, inks, sunscreens, flavoring ingredients, perfumes, cosmetics, pharmaceuticals and the like. These mesocapsules and methods of making the same disclosed herein may also be useful in the delivery of nucleic acid polymers such as double or single stranded DNA or RNA, and/or protein molecules. These formulations have a wide range of applications including genetic engineering, diagnostics and therapeutics, e.g. vaccination, and the like.

Core-shell mesocapsules can be prepared by a number of methods including interfacial polymerization at the surface of a droplet or particle. A preferred encapsulating polymer is polyurea including those formed from the reaction of a polyisocyanate with a polyamine, a poly amino acid, or water. Other preferred encapsulating polymers include those formed from melamine-formaldehyde or urea-formaldehyde condensates, as well as similar types of aminoplasts. Capsules having shell walls comprised of polyurethane, polyamide, polyolefin, polysaccaharide, protein, silica, lipid, modified cellulose, gums, polyacrylate, polyphosphate, polystyrene, and polyesters or combinations of these materials can also be used to form core-shell mesocapsules.

Suitable polymers for use in forming mesocapsules in the present disclosure include amino-based prepolymers such as urea-, melamine-, benzoguanamine-, and glycouril-formaldehyde resins and dimethyloldihydroxyethylene urea type prepolymers. These prepolymers can be used as blends and cross linkers with polyvinyl alcohol, polyvinyl amines, acrylates (acid functionality preferred), amines, polysaccharides, polyureas/urethanes, poly amino acids, and proteins. Other suitable polymers include polyesters, including biodegradable polyesters, polyamides, polyacrylates and polyacrylamides, polyvinyl polymer and copolymers with polyacrylates, polyurethanes, polyethers, polyureas, polycarbonates, naturally occurring polymers such as, polyanhydrides, polyphosphazines, polyoxazolines, and UV-cured polyolefins.

In one embodiment, a poorly water soluble agricultural active ingredient is encapsulated within a core-shell particle of very small size e.g., of about 500 nm or less, more preferably 300 nm or less. AIs encapsulated in these mesocapsules may exhibit increased penetration into insects and plants, plant tissue, plant cells and even plant pathogens than AIs that are not associated with mesocapsules.

In one embodiment the mesocapsule includes hydrophilic functional groups built into the polyurea shell and at least partially exposed on the mesocapsule's surface. A partial listing of some of the functional materials that can be used to form these particles can be found in the following publication, WO2001/94001, which is incorporated herein by reference in its entirety. Hydrophilic functional groups include carboxylate, salts of carboxylate, phosphonate, salts of phosphonate, phosphate, salts of phosphate, sulfonate, salts of sulfonate, quaternary ammonium, betaine, oxyethylene or oxyethylene-containing polymers. Preferably, the hydrophilic group is a carboxylate or the salt of a carboxylate.

In one embodiment, the agricultural active ingredient is at least one agricultural chemical selected from the group consisting of fungicides, insecticides, miticides, herbicides, safeners and modifiers of plant physiology or structure.

In one embodiment, the agricultural active ingredient has solubility in water on the order of about 1,000 parts per million or less, preferably 100 parts per million or less, and more preferably 10 parts per million or less.

In one embodiment, the invention is a method for synthesizing a mesocapsule, comprising the steps of providing an oil phase, the oil phase including at least one active ingredient and at least one polyisocyanate; supplying an aqueous phase, and adding an emulsifier; and mixing the oil and the aqueous phases under shear sufficient to form an emulsion having meso-sized droplets with a volume-average diameter of about 500 nm or less but preferably less than 300 nm; and reacting the polyisocyanate with at least one crosslinker or water to form the mesocapsule.

Some AIs are solid at room temperature and must be dissolved in a solvent before they can be encapsulated within a polyurea mesocapsule. In one embodiment a poorly water-soluble AI is dissolved in a solvent that readily dissolves the AI before adding the oil phase. Suitable solvents may be one or a mixture of organic solvents that have low water solubility, i.e. about 10 g/100 ml or less, which includes, but are not limited to, petroleum fractions or hydrocarbons such as mineral oil, aromatic solvents, xylene, toluene, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, ethylhexyl benzoate, isopropyl benzoate, n-butyl oleate, isopropyl myristate, propylene glycol dioleate, di-octyl succinate, di-butyl adipate, di-octyl phthalate, acetyl tributyl citrate, triethylcitrate, triethyl phosphate, and the like; esters of mono, di and polycarboxylic acids, such as benzylacetate, ethylacetate, and the like; ketones, such as cyclohexanone, acetophenone, 2-heptanone, gamma-butyrolactone, isophorone, N-ethyl pyrrolidone, N-octyl pyrrolidone, and the like; alkyldimethylamides, such as dimethylamide of C8 and C10, dimethylacetamide, and the like; alcohols of low water solubility (i.e. about 10 g/100 ml or less) such as benzyl alcohol, cresols, terpineols, tetrahydrofurfurylalcohol, 2-isopropylphenol, cyclohexanol, n-hexanol, and the like. In some cases, an ultrahydrophobe is added to the oil phase, ostensibly to preserve the stability of an emulsion that will be created later in the process when the oil phase is mixed with an aqueous phase. This additive is a highly water-insoluble material that 1) has a negligible diffusion coefficient and negligible solubility in the continuous aqueous phase and 2) is compatible with the dispersed phase. Examples of ultrahydrophobes include long chain paraffins such as hexadecane, polymers such as polyisobutene such as, for example, Indopol™ H15 (INESO Oligomers), polystyrene, polymethylmethacrylate, natural oils such as seed oils, and silicones such as silicone oil or dimethicone. Preferably, the additive is used in an amount not greater than 10 weight percent based on the weight of the dispersed phase.

In one embodiment, the polymer precursor within the dispersed phase is a polyisocyanate or a mixture of polyisocyanates. The polyisocyanate reacts with a crosslinker or with water to form a polyurea shell. Examples of polyisocyanates include, but are not limited to, toluene diisocyanate (TDI), diisocyanato-diphenylmethane (MDI), derivatives of MDI such as polymethylene polyphenylisocyanate that contains MDI, an example of which is PAPI 27™ polymeric MDI (The Dow Chemical Company), isophorone diisocyanate, 1,4-diisocyanatobutane, phenylene diisocyanate, hexamethylene diisocyanate, 1,3-bis(isocyanatomethyl)benzene, 1,8-disocyanatooctane, 4,4'-methylenebis(phenyl isocyanate), 4,4'-methylenebis(cyclohexyl isocyanate) and mixtures thereof. In another embodiment, suitable polymer precursors in the dispersed phase may also include but are not limited to diacid chlorides, polyacid chlorides, sulfonyl chlorides, chloroformates, and the like, and mixtures thereof.

The oil and water phases are combined in the presence of a surfactant that aids in the creation and or stabilization of meso-size droplets of less than 500 nm but preferable less than 300 nm. The surfactant can be added to either the oil phase or to the water phase or to both the oil and water phases. Surfactants include nonionic, anionic, cationic, or combinations of nonionic and anionic or nonionic and cationic. Examples of suitable surfactants include alkali metal lauryl sulfates such as sodium dodecyl sulfate, alkyl metal fatty acids salts such as oleates and stearates, alkali methyl alkylbenzene sulfonates such as sodium dodecylbenzene sulfonate, polyoxyethylene nonionics, and quaternary ammonium surfactants. Standard reference sources from which one of skill in the art can select suitable surfactants, without limitation to the above mentioned classes, include Handbook of Industrial Surfactants, Fourth Edition (2005) published by Synapse Information Resources Inc, and McCutcheon's Emulsifiers and Detergents, North American and International Editions (2008) published by MC Publishing Company.

The emulsion can be prepared by a variety of methods, including batch and continuous methods well known in the art. In a preferred method, the emulsion is prepared using an ultra-high shear device such as an ultrasonicating device or a high-pressure homogenizer to create meso-size droplets of less than 500 nm, preferably less than 300 nm. Ultrasonicating devices include standard sonicating equipment containing a ultrasonic probe that is inserted into the formulation to create the meso-size droplets, one representative example being the Sonicator 400 from Misonix Sonicators. High-pressure homogenizers use very high pressure, 500 to 20,000 psi, to force fluid through a small opening and create the meso-size droplets. Examples of such devices include but are not limited the EmulsiFlex™ (Avestin, Inc.) devices and the Microfluidizer™ (Microfluidics) devices.

In one embodiment a polyisocyanate or a mixture of polyisocyanates reacts with hydroxyl-containing or amine-containing molecules in the continuous phase (i.e. water), such as water-soluble diamines, water soluble polyamines, water soluble polyamino acids, water soluble diols, water soluble polyols, and mixtures thereof, via an interfacial polycondensation to form a polymeric shell. Examples of these chain extenders or cross-linkers in the aqueous continuous phase may include, but are not limited to, at least one of water soluble diamines, such as ethylenediamine, and the like; water soluble polyamines, such as diethylenetriamine, triethylenetetramine, tetraethylenepentamine, pentaethylenehexamine, and the like; water soluble amino acids having more than one isocyanate-reactive functional group, such as L-lysine, arginine, histidine, serine, threonine, polymers or oligomers of these aminoacids, and the like; water soluble diols or water soluble polyols, such as ethylene glycol, propylene glycol, polyethylene oxide diol, resorcinol, water soluble amino alcohols, such as 2-aminoethanol, and the like, and guanidine, guanidine compounds, polyamidines and derivatives and mixtures thereof. In one embodiment the water soluble phase includes a diamine with a carboxylate functionality (such as L-lysine) which reacts to form a polyurea shell that includes carboxylate functional groups at the surface of the mesocapsule. This carboxylate functionality may be unneutralized or it may be partly or fully neutralized to form a carboxylate salt.

In still another embodiment the diamine or polyamines or their equivalents, included in the aforementioned exemplary aqueous phase, are omitted from the reaction mixture. In this embodiment the polyisocyanate reacts with water to form a polyurea shell.

Various factors can be adjusted to increase or decrease the interfacial condensation reaction rate. These factors include, for example, temperature, pH, mixing rate, reaction times, osmotic pressure and of course changing the levels and types of emulsifiers, polymer components, solvents, the addition of catalysts and the like. For an additional discussion of the effect on temperature, catalysts, pH and the like on these types of reactions see for example U.S. Pat. No. 4,285,750, which is incorporated herein by reference in its entirety. Additional information on the effect of salts and salt levels on these types of reactions can be found in publication, WO2006/092409, which is incorporated herein by reference in its entirety.

Some embodiments of the present disclosure can be realized by varying the levels of some of the reactants in the reaction mixture, the reaction mixture consisting of a dispersed oil phase and a continuous aqueous phase which are used to form mesocapsules that include at least one AI. In some embodiments these include, given as weight percent (wt. %) of the oil phase of at least one AI in the range of from about 1.0 wt. % to about 90 wt. %, more preferably from about 1.0 wt. % to about 80 wt. %; optionally, a solvent suitable for dissolving the AI in the range of from about 1 wt. % to about 90 wt. %, more preferably from about 20 wt. % to about 80 wt. %; optionally, an ultrahydrophobe present in the range of from about 0.5 wt. % to about 10 wt. %, more preferably from about 1.0 wt. % to about 5.0 wt. %; at least one polyisocyanate present in the range of from about 1 wt. % to about 30 wt. %, more preferably from about 5 wt. % to about 20 wt. %; optionally, an emulsifier present in the range of from 0.1 wt. % to about 20 wt. %, more preferably from about 1 wt. % to about 10 wt. % of the oil phase, in which the oil phase makes up on the order of from about 1% to about 60% of the total amount of the emulsion.

The aqueous phase of the reaction mixture consists of from about 40 wt. % to about 99 wt. % of the total emulsion and contains from about 60 wt. % to about 90 wt. % water, from about 1 wt. % to about 30 wt. % of one or more cross-linkers and optionally, from about 0.1 wt. % to about 20 wt. % of one or more water soluble surfactants.

Similarly, some of the ingredients used in some of the exemplary formulations are optional. For example, it is possible to synthesize effective mesocapsules in some embodiments without adding the solvent and/or the ultrahydrophobe. The addition of these types of optional components to the reaction mixture is especially useful when the AI is a solid.

As described herein, one method used in encapsulating poorly water-soluble materials is to create a polyurea core-shell by an interfacial condensation reaction of a polyisocyanate or a mixture of polyisocyanates in the dispersed oil phase with at least one of water and a water-soluble polyamine in the continuous phase. In order to stabilize the microcapsule against agglomeration and to control the size of microcapsule before the reaction, it is often desirable to add one or more surfactants or colloidal stabilizers to the reaction mixture. A surfactant may be useful if the goal of the reaction is to create mesocapsules smaller than 500 nm. However, the presence of surfactant may be detrimental in many end use applications. For example, in delivery of agricultural active ingredients into a plant, the surfactant accompanying the polyurea mesocapsules may be injurious to the plant. In other applications, the surfactant may also cause unwanted foaming in the final product. Accordingly, it may be beneficial to develop a method for efficiently synthesizing micro- and mesocapsules that required less or no surfactant than the methods previously discussed.

One aspect of the present disclosure is a method for producing microcapsules or mesocapsules in which a compound is added that includes at least one functional moiety that is either a primary or secondary amine or a primary or secondary amino group and additionally at least one hydrophilic functional group, and wherein the addition of this component allows for an emulsion to be made with essentially no surfactant. In one embodiment of the invention, the component is glycine, a salt of glycine, or a mixture of glycine and a salt of glycine. These methods for producing micro- or mesocapsules include adding glycine, a salt of glycine, or a mixture of glycine and a salt of glycine to the aqueous phase of the reaction mixture before creating the final emulsion, and, if desired, before initiating the cross linking reaction between components such as polyisocyanate to create the polyurea mesocapsules shell. Additional molecules that can be used in addition to or in place of glycine include other molecules that have either a primary or secondary amine group on one end and of the molecule and a hydrophilic group such as a carboxylate or a trimethylamine on the other end of the molecule. It may not be necessary to neutralize all of the charged moieties in order to obtain the product formed by the processes disclosed herein. A partial list of some of these types of molecules can be found in U.S. Pat. No. 4,757,105 which is incorporated herein by reference in its entirety.

Without wishing to be bound by any single theory or explanation it may be that adding either the glycine, a glycine salt, or glycine-like material before forming the final emulsion allows the glycine to react with a small part of the di- or polyisocyanate to create a surfactant-like molecule which aids in the creation and/or the stabilization of the emulsion and helps control the droplet size in the final emulsion. Next, after creation of the final emulsion, during the interfacial condensation reaction, the surfactant-like molecule formed by the reaction of glycine reacts to become incorporated into the polyurea shell and no longer acts as a free surfactant. The hydrophilic functional group of the glycine or glycine like molecule exists at the surface of the shell to help stabilize the shell.

The present disclosure includes a method for encapsulating poorly water-soluble AIs within a polyurea core-shell particle using reduced levels of surfactant or colloidal stabilizer or by using no surfactant or colloidal stabilizer and still maintaining dispersion stability and particle size control. This present disclosure has applications in delivering agricultural active ingredients where excess surfactant could have phytotoxic effects on plants and for other delivery or controlled release applications where the presence of a surfactant would be detrimental in the final application.

Polyurea meso-capsules can be made without surfactant using colloidal stabilizers such as polyvinyl alcohol but it is difficult to control particle size. Some formulations of AIs are made using surfactants that do not exhibit some of the properties that need to be avoided, such as using less phytotoxic surfactants or surfactants that exhibit less foaming.

Adding a glycine salt or a similar molecule that includes either primary or secondary amine groups and either a carboxylate group or a trimethylamine to the aqueous phase before creating the final emulsion lowers or eliminates altogether the need to add a surfactant to the reaction mixture. Adding a material that is not a surfactant such as glycine and that reacts with the di- or polyisocyanate to create a molecule that helps to emulsify and stabilize the organic phase and that further reacts into polyurea shell once the di or polyisocyanate, enables the production of mesocapsules that are free or essentially free of surfactants. In some embodiments essentially free implies that the oil phase includes less than about 1.0 weight percent and more preferably less than 0.5 weight percent of a surfactant.

Being able to formulate mesocapsules that include no or very little residual surfactant has advantages in many applications where the presence of free surfactant in the formulation has a detrimental or unwanted effect. There may also be a potential cost advantage in case the amount of expensive surfactant can be reduced.

One embodiment of the invention is a mesocapsule that includes at least one AI such as, for example, the fungicide fenbuconazole. An exemplary method of forming these mesocapsules includes an interfacial polycondensation reaction between the compound in the oil phase and either water or water and a water soluble cross linker in the aqueous phase. In order to produce mesocapsules, especially mesocapsules with an average diameter of about 500 nm or less or mesocapsules with an average diameter of about 300 nm or less, either a surfactant such as sodium dodecyl sulfate can be added to the reaction mixture or a molecule such as glycine can be added to the aqueous phase before creating the final emulsion and/or initiating the cross linking reaction. In one embodiment the oil and aqueous phases are mixed under high-shear to form an emulsion that includes meso-sized droplets which are converted into polyurea mesocapsules as described herein. Devices for processing the emulsion to help form mesocapsules include ultrasonicating devices and/or high-pressure homogenizers. Ultrasonicating devices include standard sonicating equipment containing an ultrasonic probe that is inserted into the system to create the meso-size droplets, one representative example being the Sonicator 400 from Misonix Sonicators. High-pressure homogenizers use very high pressure, 500 to 20,000 psi, to force fluid through a small opening and create the meso-size droplets. Examples of such devices include the EmulsiFlex™ (Avestin, Inc.) devices and the Microfluidizer™ (Microfluidics) devices.

In one embodiment a poorly water soluble AI is optionally dissolved in a solvent such as benzyl acetate. Optionally, an ultrahydrophobe such as hexadecane can be added to help preserve the stability of an emulsion that will form once the oil and water phases are combined. A polyisocyanate, for example PAPI™ 27 polymeric MDI (The Dow Chemical Company) is added to the oil phase. In order to aid in the formation of meso-sized droplets which are a precursor to forming mesocapsules a surfactant such as the sodium salt of dodecyl sulphate (SDS) may be added to either or both the oil or water phases. Alternatively, glycine or any other molecule with either an amine or amino moiety on one end of the molecule and a hydrophilic group on the other end of the molecule is added to the aqueous phase before forming the final emulsion or initiating the cross-linking reaction. The amount of glycine or similar molecule can be increased as necessary to replace all or at least some of the surfactant. Next, the oil and water phases are mixed and optionally processed with an ultra-high shear device such as a Microfluidizer™ (Microfluidics) device to create the desired small droplets, which are converted to mesosized polyurea capsules as described herein.

Many classes and types of insecticides are useful in agriculture and pest management. Examples include insecticides such as antibiotic insecticides such as allosamidin and thuringensin, macrocyclic lactone insecticides such as spinosad, spinetoram and 21-butenyl spinosyns; avermectin insecticides such as abamectin, doramectin, emamectin, eprinomectin, ivermectin and selamectin; milbemycin insecticides such as lepimectin, milbemectin, milbemycin oxime and moxidectin; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, paradichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as imicyafos and mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; ryanodine receptor insecticides such as flubendiamide, chlorantraniliprole (rynaxypyr) and cyantraniliprole; tetronic acid insecticides such as spirodiclofen, spiromesifen and spirotetramat; thiourea insecticides such as diafenthiuron; urea insecticides such as flucofuron and sulcofuron; sulfoximine insecticides such as sulfoxaflor and unclassified insecticides such as closantel, crotamiton, EXD, fenazaflor, fenazaquin, fenoxacrim, fenpyroximate, flubendiamide, hydramethylnon, isoprothiolane, malonoben, metaflumizone, metoxadiazone, nifluridide, pyridaben, pyridalyl, pyrifluquinazon, rafoxanide, triarathene and triazamate. The present invention contemplates selecting insecticides from this list with water solubilities of about 1000 ppm or less and formulating them as core-shell polyurea meso-capsules. Preferable insecticides are those with water solubilities of about 100 ppm or less. More preferable insecticides are those with water solubilities of 10 ppm or less. Insecticides can be chosen based on water solubilities published in compendia such as The Pesticide Manual Fourteenth Edition, (ISBN 1-901396-14-2), which is incorporated herein by reference in its entirety. Future editions of The Pesticide Manual will also be useful for selecting insecticides for incorporation into core-shell polyurea meso-capsules.

Many classes and types of fungicides are useful in agriculture. Examples include, ametoctradin, amisulbrom 2-(thiocyanatomethylthio)-benzothiazole, 2-phenylphenol, 8-hydroxyquinoline sulfate, antimycin, azaconazole, azoxystrobin, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, BYF 1047, calcium polysulfide, captafol, captan, carbendazim, carboxin, carpropamid, carvone, chloroneb, chlorothalonil, chlozolinate, copper hydroxide, copper octanoate, copper oxychloride, copper sulfate, copper sulfate (tribasic), cuprous oxide, cyazofamid, cyflufenamid, cymoxanil, cyproconazole, cyprodinil, coumarin, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, meptyl dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutolanil, flutriafol, fluxapyrad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, meptyldinocap, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, penflufen, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyraxostrobin, pyrazophos, pyribencarb, pyributicarb, pyrifenox, pyrimethanil, pyriofenone, pyrometostrobin, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-048, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazolopyrimidine, triazoxide, tricyclazole, tridemorph, trifloxystrobin, triflumizole, triforine, triticonazole, validamycin, valiphenal, valifenate, vinclozolin, zineb, ziram, zoxamide, (RS)—N-(3,5-dichlorophenyl)-2-(methoxymethyl)-succinimide, 1,2-dichloropropane, 1,3-dichloro-1,1,3,3-tetrafluoro acetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, UK-2A, derivatives of UK-2A such as, for example, (3S,6S,7R,8R)-8-benzyl-3-(3-(isobutyryloxymethoxy)-4-methoxypicolinamido)-6-methyl-4,9-dioxo-1,5-dioxonan-7-yl isobutyrate which has a CAS Registry Number of 328255-92-1 and will be referred to herein as 328255-92-1, urbacid, XRD-563, and zarilamid, IK-1140, and propargyl amides. The present invention contemplates selecting fungicides from this list with water solubilities of about 1000 ppm or less and formulating them as core-shell polyurea meso-capsules. Preferable fungicides are those with water solubilities of about 100 ppm or less. More preferable fungicides are those with water solubilities of 10 ppm or less. Fungicides can be chosen based on water solubilities published in compendia such as The Pesticide Manual Fourteenth Edition, ISBN 1-901396-14-2, which is incorporated herein by reference in its entirety. Future editions of The Pesticide Manual will also be useful for selecting fungicides for incorporation into core-shell polyurea meso-capsules.

Many classes and types of herbicides are useful in agriculture. Examples include amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, fluroxypyr-meptyl, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. The present invention contemplates selecting herbicides from this list with water solubilities of about 1000 ppm or less and formulating them as core-shell polyurea meso-capsules. Preferable herbicides are those with water solubilities of about 100 ppm or less. More preferable herbicides are those with water solubilities of 10 ppm or less. Herbicides can be chosen based on water solubilities published in compendia such as The Pesticide Manual Fourteenth Edition, ISBN 1-901396-14-2, which is incorporated herein by reference in its entirety. Future editions of The Pesticide Manual will also be useful for selecting herbicides for incorporation into core-shell polyurea mesocapsules.

Many classes and types of modifiers of plant physiology and structure are useful in agriculture. Examples include ancymidol, aminoethoxyvinylglycine, 6-benzylaminopurine, carvone, chlorflurenol-methyl, chlormequat chloride, cloxyfonac, 4-CPA, cyclanilide, cytokinins, daminozide, dikegulac, ethephon, flurenol, flurprimidol, forchlorfenuron, gibberellic acids, gibberellins, inabenfide, indol-3-ylacetic acid, 4-indol-3-ylbutyric acid, maleic hydrazide, mepiquat chloride, 1-methylcyclopropene, 2-(1-napthyl)acetamide, 1-napthylacetic acid, 2-napthyloxyacetic acid, nitrophenolates, paclobutrazol, N-phenylphthalamic acid, prohexadione-calcium, n-propyl dihydrojasmonate, thidiazuron, tribufos, trinexepac-ethyl, and uniconazole. The present invention contemplates selecting growth regulators from this list with water solubilities of about 1000 ppm or less and formulating them as core-shell polyurea meso-capsules. Preferable modifiers of plant physiology and structure are those with water solubilities of about 100 ppm or less. More preferable modifiers of plant physiology and structure are those with water solubilities of 10 ppm or less. Modifiers of plant physiology and structure can be chosen based on water solubilities published in compendia such as The Pesticide Manual Fourteenth Edition, ISBN 1-901396-14-2, which is incorporated herein by reference in its entirety. Future editions of The Pesticide Manual will also be useful for selecting modifiers of plant physiology and structure for incorporation into core-shell polyurea mesocapsules.

Mesocapsule formulations of herbicides in accordance with various embodiments can be used in combination with a wide variety of herbicide safeners, incuding safeners such as benoxacor, benthiocarb, bras sinolide, cloquintocet (mexyl), cyometrinil, cyprosulfamide, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenylsulfonylbenzoic acid amides. The level of active ingredient level in the oil phase used to synthetize these formulations can range from about 0.001 wt. % to about to 99 wt. %. The safeners may be encapsulated in core-shell mesocapsules alone or incombination with suitable herbicides or they may be added to the formulation medium outside of the meso-capsule.

It is contemplated that mesoparticles of the present disclosure can be used with many conventional formulation ingredients such as aqueous or non-aqueous solvent media or diluents in which the mesoparticles are suspended or slurried at a concentration of the agricultural active ingredient, with respect to the formulation, from about 0.1% to about 30%. Conventional inactive or inert ingredients such as dispersants, thickening agents, stickers, film-forming agents, buffers, emulsifiers, anti-freeezing agents, dyes, stablizers, solid carriers and the like may also be incorporated into formulations containing mesoparticles.

It is contemplated that formulations of agricultural AIs contained in mesocapsules can be utilized to control insects, mites, plant diseases or weeds by providing and applying an agriculturally effective amount of the formulation to at least one of the following: the plant, plant foliage, blossoms, stems, fruits, the area adjacent to the plant, soil, seeds, germinating seeds, roots, liquid and solid growth media, and hydroponic growth solutions, surface to be treated, and into or onto the pest itself. The mesocapsule formulation can be diluted in a suitable agricultural diluent, such as water, and applied by any conventional method, including but not limited to: 1) application as a foliar spray, preferably in sufficient volume to wet the foliage or treatment surface, 2) application as a drench to soil, 3) application to seeds, 4) application by injection into soil or hydroponic growth media, and 5) directly into or onto the pest. It is further envisioned that mesocapsule formulations can be applied in mixture with conventional formulations of agricultural AIs, plant nutrients and modifiers of plant physiology and structure. Conventional formulations of agricultural AI's include solutions such as oil in water or water in oil emulsifiable concentrates and dispersions, solutions of AIs in water, sprayable concentrates of AIs as suspended particulates with a volume average diameter of about 1 micron or larger, AIs in the form of wettable powders with a volume average diameter of about 1 micron or larger and AIs in the form of granules with a volume average diameter of about 10 microns or larger.

EXAMPLES

Particle Size Measurements

The particle size can be determined in particular by the known method of quasi-elastic light scattering. One apparatus that can be used for this determination is the Brookhaven 90Plus Nanoparticle Size Analyzer. This apparatus provides a measure of the average diameter by photon correlation spectroscopy (or PCS). In addition, the Malvern MasterSizer 2000 may also be used for particle size measurements. Alternatively, particle size may be measured by other known techniques including centrifugation or electron microscopy.

Synthesis of Mesocapsules

Preparation of Stock Solutions of Amino Acids Used to Synthesize Mesocapsules.

Before the initiation of the various reaction runs used to synthesize the exemplary mesocapsules disclosed herein, stock solutions of glycine and lysine were prepared in the proportions listed in FIG. 1.

General Methods Used to Prepare Some of the Polyurea Mesocapsules Disclosed Herein.

A typical method used to synthesize a representative polyurea mesocapsule formulation is set forth below using the ingredients and quantities listed in FIG. 2. Briefly, fenbuconazole, benzyl acetate, hexadecane, and PAPI™ 27 polymeric MDI (The Dow Chemical Co.) were added to a 60 ml jar and mixed until uniform. Surfactant, water, and glycine solutions were added to the jar and mixed with a hand-held BioHomogenizer mixer (BioSpec Products, Inc.) for about 10 seconds to create a pre-emulsion. The jar was placed in an ice bath and the pre-emulsion was sonicated for 5 minutes using a Branson 184V Ultrasonicator at 40% power to create the final emulsion. A crosslinker was added to final emulsion to react with the polymeric MDI to create the final product except for sample 4 in which the polymeric MDI was allowed to react with water over time to create the final product. The particle volume-average diameter of meso-capsules in each sample was measured using a Brookhaven 90Plus Nanoparticle Size Analyzer. The various mesocapsule formulations listed in FIG. 2 were made using these methods. As indicated in FIG. 2, the compositions of the reaction mixtures were varied to create the various formulations disclosed herein. The formulations referenced in FIG. 4 were tested on plants to determine their curative and preventative plant disease control properties.

A polyurea mesocapsule formulation containing fenbuconazole was prepared using the ingredients described herein as wt % amounts relative to the entire formulation. The oil phase and aqueous phase were prepared separately. In the oil phase were combined, 5.07 wt % of fenbuconazole, 14.33 wt % of cyclohexanone and 14.08 wt % of Aromatic 200 solvent to provide an initial solution. To the initial solution were added 1.31 wt % of Indopol™ H15 (INEOS Oligomers), 6.54 wt % of isophorone diisocyanate and 2.18 wt % of PAPI™ 27 (The Dow Chemical Company). In the aqueous phase were combined 42.56 wt % of water, 0.10 wt % of Proxel™ GXL (Arch UK Biocides, Ltd.) and 0.44 wt % of sodium lauryl sulfate. The aqueous phase was combined with the oil phase while mixing with a Silverson L4RT High Shear Mixer/Emulsifier at 6000 rpm for 2 min to make a pre-emulsion that was cooled in an ice/water bath. The pre-emulsion was subsequently homogenized under high pressure with ice/water cooling by an Emulsiflex®-C3 (Avestin, Inc., 600-1000 bar) to make a stable oil-in-water emulsion at meso scale. With stirring, 0.87 wt % of solid sodium lauryl sulfate was added, followed by the addition of 1.31 wt % of L-lysine (dry weight basis) as a 44.4 wt % solution in water to react with PAPI™ 27, and the addition of 2.20 wt % of diethylenetriamine as a 25 wt % solution in diethylene glycol-water (0.76:0.24, wt %/wt %) in 1 hr to react with the isophorone diisocyanate. The mixture was allowed to stir at room temperature for 4 hr to complete polyurea shell formation. The formulation contained mesocapsules of fenbuconazole with a particle volume average diameter of 313 nm.

The following procedures were utilized to make mesocapsule suspensions of 328255-92-1, epoxiconazole, atrazine, fluoroxypyr-meptyl, spinosad and indoxacarb. The oil phase and aqueous phase were prepared separately using the ingredients and amounts shown in FIG. 3. The active ingredient was dissolved in solvent/solvent mixtures to make 77% of the oil phase, followed by the addition of 3% ultrahydrophobe and 20% isocyanate (Monomer 1). Into the aqueous phase were added Proxel™ GXL (Arch UK Biocides, Ltd.; 0.1% of total formulation) and sodium lauryl sulfate (3% of oil phase). The aqueous phase was combined with the oil phase and the mixture was magnetically stirred for 2 min to make a pre-emulsion, which was subsequently sonicated (4-5 min) using a Vibra Cell™ (Sonics & Materials, Inc.) sonicator at 750 W and 24-25% amplitude in an ice/water bath to make a stable oil-in-water emulsion at meso scale. Upon stiffing, polyamine (Monomer 2) was added to react with the isocyanate to form the polyurea shell. The various mesocapsule formulations listed in FIG. 3 were made using these methods. The formulations referenced in FIG. 4 were tested on plants and insects to determine their pest control properties.

Aqueous suspension concentrate formulations of 328255-92-1, epoxiconazole and indoxacarb were prepared by conventional methods using standard surfactants, wetting agents and milling equipment to provide samples 7, 9 and 13 shown in FIG. 4. These samples had volume average diameters of about 2.5 μm each.

Referring now to FIG. 4, the table includes a listing of some of the formulations that were tested on wheat leaf blotch. The polyurea mesocapsules of fenbuconazole listed in FIG. 4 were tested to measure their curative and protectant effects on wheat leaf blotch disease, which is caused by the fungus, *Septoria tritici*. Measurements were conducted on separate sets of wheat (cultivar Yuma) plants. The polyurea mesocapsules made in accordance with various embodiments disclosed herein were compared to Indar™ 75WP, a commercially available formulation of fenbuconazole. Each formulation of fenbuconazole was diluted in water and tested at the rates of 62.5, 20.8, 6.9, 2.3 and 0.77 g active ingredient/Ha. Each experimental unit consisted of 8 to 10 wheat plants grown in 5 cm by 5 cm pots of growth media comprised of half MetroMix and half clay loam soil. Each treatment was replicated three times and treatments were randomized after chemicals were applied.

In the curative test, plants were inoculated in the 2-leaf stage of growth two days before the test and control formulations were applied to the plants. For the protectant test, the test and control formulations were applied to the plants during the two leaf stage of growth and inoculated four days later with the fungi that causes leaf blotch disease. Treatments were applied using a Gen III Research Sprayer (DeVries Mfg., Hollandale Minn.) tracksprayer equipped with a Spraying Systems 8002E TeeJet spray nozzle and calibrated to deliver 100 L/Ha.

Inoculum of the foliar pathogen, *Septoria tritici*, was prepared by harvesting conidia from freshly erumpent and mature pycnidia. An aqueous suspension of conidia was made by counting several samples in a haemocytometer and then adjusting the suspension to include about 1,000,000 conidia/ml. Plants were inoculated by applying a fine mist with a low pressure compressed air sprayer at a volume of approximately 200 ml per 80 pots of wheat. After inoculation, plants were incubated in a dark dew room (22° C.) at 99-100% relative humidity for 24 hours, then moved to a lighted dew room (20° C.) at 99-100% relative humidity for an additional 48 hrs and then placed in a greenhouse set at 20° C. and a 14-hr photoperiod for the remainder of the test. Plant growth was maintained through regular application of dilute liquid fertilizer solution.

The wheat seedlings were rated for disease about 21 days after the inoculation. Percent disease was assessed by making a visual estimate of the percent of the leaf showing disease symptoms. Plants that were first inoculated and then treated with chemical two days later provided indications of curative effects. Plants that were first treated and then inoculated four days later provide indications of protectant effects. The disease level measured on untreated plants in the curative test was about 82%. The disease level measured on untreated plants in the protectant test was about 95%.

Referring now to FIGS. 5 and 6, the results of the various tests are as follows. In the curative test (FIG. 5), all mesocapsule formulations of fenbuconazole resulted in generally lower levels of disease when compared to the standard wettable powder formulation of fenbuconazole. Similarly, in the protectant test (FIG. 6), mesocapsule formulations of fenbuconazole resulted in lower levels of disease at one or more rates tested when compared to the standard wettable powder formulation.

Referring now to FIG. 4, the table includes a listing of some of the formulations that were tested on brown rust of wheat. The polyurea mesocapsule formulations of 328255-92-1 and epoxiconazole listed in FIG. 4 were tested to measure their protectant effects on the wheat disease known as brown rust, which is caused by the fungus, *Puccinia recondita* f. sp. *tritici*. Measurements were conducted on wheat (cultivar Yuma) plants. The polyurea mesocapsules made in accordance with various embodiments disclosed herein were compared to conventional water-based particulate formulations. Each formulation was diluted in water and tested at the rates of 62.5, 20.8, 6.9, 2.3 and 0.77 g active ingredient/Ha. Each experimental unit consisted of 8 to 10 wheat plants grown in 5 cm by 5 cm pots of growth media comprised of half MetroMix and half clay loam soil. Each treatment was replicated four times and treatments were randomized after chemicals were applied.

The test and control formulations were applied to the plants during the two leaf stage of growth and inoculated four days later with the brown rust fungus. Treatments were applied using a Gen III Research Sprayer (DeVries Mfg., Hollandale Minn.) tracksprayer equipped with a Spraying Systems 8002E TeeJet spray nozzle and calibrated to deliver 100 L/Ha.

Inoculum of the foliar pathogen, *Puccinia recondita* f.sp. *tritici*, was prepared by harvesting urediospores from freshly erumpent and mature pustules. The final aqueous suspension of urediospores was made using the following procedure. 0.1 g of urediospores, added to three drops of Tween 20, and then mixed as a paste. To the paste was added 100 ml of distilled water. The suspension yielded approximately 1,000,000 urediospores/ml. Plants were inoculated by applying a fine mist with a low pressure compressed air sprayer at a volume of approximately 300 ml per 80 pots of wheat. After inoculation, plants were incubated in a dark dew room (22° C.) at 99-100% relative humidity for 24 hr, then moved to a greenhouse set at 24° C. and a 14-hr photoperiod for the remainder of the test. Plant growth was maintained through regular application of dilute liquid fertilizer solution.

The wheat seedlings were rated for disease approximately 7-8 days after the inoculation. Percent disease was assessed by making a visual estimate of the percent disease on the primary leaf. Results were averaged across rates. The test was performed twice and results of the individual tests were combined.

Referring now to FIG. 7, the combined results of two protectant tests with brown rust indicate that mesocapsule formulations of 328255-92-1 and epoxiconazole resulted in generally lower levels of disease when compared to the standard sprayable concentrate formulations.

Referring now to FIG. 4 the table includes a listing of the formulations that were tested for the herbicidal active ingredients atrazine and fluoroxypyr-meptyl. The polyurea meso-formulations made in accordance with various embodiments disclosed herein were compared to conventional water-based particulate formulations. The polyurea mesocapsule formulations of atrazine and fluoroxypyr-meptyl listed in FIG. 4 were tested to measure their post-emergence herbicidal effects on various dicot and monocot weed species utilizing the methods described herein.

A peat based potting soil, Metro-mix 360, was used as the soil media for this test. Metro-mix is a growing medium consisting of 35 to 45% specially processed coconut coir pith, 10 to 20% horticultural grade vermiculite, 15 to 25% processed ash bark, 20 to 30% choice Canadian Sphagnum Peat Moss and proprietary nutrients and other ingredients. Several seeds of each species were planted in 10 cm square pots and top watered twice daily. *Casia obtusifolia* (CASOB), *Abutilon theophrasti* (ABUTH), *Sida spinosa* (SIDSP), *Setaria faberi* (SETFA), *Digitaria sativa* (DIGSA), *Kochia scoparia* (KCHSC), *Stellaria media* (STEME), *Polygonum convolvulus* (POLCO), *Chenopodium album* (CHEAL) and *Ambrosia artemisiifolia* (AMBEL) were propagated in the greenhouse at a constant temperature of 26 to 28° C. and 50 to 60% relative humidity. Natural light was supplemented with 1000-watt metal halide overhead lamps with an average illumination of 500 uE m-2 s-1 photosynthetic active radiation (PAR). The photoperiod was 16 hr. Plant material was top-watered prior to treatment and sub-irrigated after treatment.

The mesocapsule formulation of atrazine was compared to a standard water dispersable granule commercial formulation, AAtrex Nine-0™ (Syngenta). The two formulations of atrazine were diluted in de-ionized water and applied at the rates of 2240, 1120, 460 and 280 g active ingredient/Ha. The mesocapsule formulation of fluoroxypyr-meptyl was compared to a standard commercial fluoroxypyr-meptyl formulation, Casino™ 25WP (Dow AgroSciences, LLC). The two formulations of fluoroxypyr-meptyl were diluted in de-ionized water and applied at the rates of 200, 100, 50, 25 and 12.5 g active ingredient/Ha. Treatments were applied with a tracksprayer manufactured by Allen Machine Works. The sprayer utilized an 8002E spray nozzle, spray pressure of 262 kPa pressure and speed of 1.5 mph to deliver 187 L/Ha. The nozzle height was 46 cm above the plant canopy. The growth stage of the various weed species ranged from 2 to 4 leaf. Treatments were replicated 3 times. Plants were returned to the greenhouse after treatment and sub-watered throughout the duration of the experiment. Plant material was fertilized twice weekly with Hoagland's fertilizer solution. Visual assessments of percent control were made on a scale of 0 to 100% as compared to the untreated control plants (where 0 is equal to no control and 100 is equal to complete control).

Referring now to FIG. 8 the results of the post-emergence herbicide test indicate that mesocapsule formulation of atrazine resulted in generally higher levels of control when compared to the standard water dispersable granule formulation.

Referring now to FIG. 9 the results of the post-emergence herbicide test indicate that mesocapsule formulation of fluoroxypyr-meptyl resulted in generally higher levels of control when compared to the standard wettable powder formulation.

Referring now to FIG. 4, the table includes a listing of the formulations that were tested for the insecticidal active ingredient indoxacarb. The polyurea mesocapsule formulation of indoxacarb (Sample 12) listed in FIG. 4 was tested to measure the effects on $2^{nd}$ instar diamondback moth larvae (*Plutella xylostella*) and male adult German cockroach (*Blatella germanica*) mortality and leaf disk or bait consumption, respectively. The indoxacarb polyurea mesocapsule formulation made in accordance with various embodiments disclosed herein was compared to a suspension concentrate water based formulation of indoxacarb (Sample 13).

Each formulation of indoxacarb was diluted in water for testing. Rates tested for mortality and treated leaf disk consumption for diamondback moth were 0.15, 0.62, 2.5, 10, 20, 40, 80, and 160 ppm. Rates tested for mortality and treated water based bait for German cockroach were 0.0001%, 0.001%, 0.01%, 0.1%, and 1% depending on the type of test (ie injection, topical application or ingestion of water based bait).

For the Diamondback moth test, cabbage plants were grown in the greenhouse and were trimmed to 2 leaves per plant. Formulations were diluted using deionized water plus addition of 0.025% Silwet L-77 surfactant. Tested rates were 0.15, 0.62, 2.5, 10, 20, 40, 80, and 160 ppm. Cabbage plants were sprayed using a track sprayer delivering approximately 200 liters/hectare spray volume. After the treated cabbage plants dried, leaf discs were taken from each sprayed plant and 1 leaf disk was placed in each well of a 32 well bioassay tray which contained a thin layer of agar at the bottom of the well. Three $2^{nd}$ instar diamondback moth larvae were placed in the center of each leaf disc and the tray was covered with a plastic lid. Data on mortality and percent leaf disk consumed was collected at various time intervals from 1-4 days.

Referring now to FIGS. 10 and 11, the results of the diamondback moth test are as follows. Differences were noted in favor of the polyurea mesocapsule formulation at the rates of 2.5 and 10 ppm.

At the 2.5 ppm rate, the polyurea mesocapsule formulation treatment reduced the amount of treated leaf disc consumption by 28-46 percent at 3 and 4 days post-treatment, respectively, as compared to the water based suspension concentration formulation treatment. At the 10 ppm rate, the polyurea meso-formulation treatment reduced the amount of treated leaf disc consumption by 18-37% at 3 and 4 days post-treatment, respectively, as compared to the water based suspension concentration formulation treatment. This decreased amount of treated leaf disk consumption indicates the indoxacarb polyurea mesocapsule formulation was able to protect the treated cabbage plant from feeding by diamondback moth larvae better than a water based suspension concentration formulation of indoxacarb.

At the 10 ppm rate at 4 days post-treatment, the polyurea mesocapsule formulation treatment increased the amount of diamondback moth larvae mortality 19% as compared to the water based suspension concentration formulation treatment. This increased mortality indicates the indoxacarb polyurea meso-formulation was able to enhance toxic activity at the 10 ppm rate over the water based suspension concentration formulation of indoxacarb.

Three types of tests were conducted for German cockroach—injection, topical and ingestion bioassay. For the injection test, 10 male adult German cockroachs per treatment were injected with 1 ul of each treatment. Treatments solutions were made by diluting indoxacarb formulations in Milli-Q purified water to produce indoxacarb concentrations of 0.001%, 0.01%, 0.1% and 1%. The injected cockroaches were held in 100×25 mm petri dishes containing food and water and placed in a laboratory controlled environment chamber at 26° C. and 60% relative humidity. The injected cockroaches were checked daily for 7 days and the number dead were recorded. Food and water was refreshed as needed.

Referring now to FIG. 12, the results of the German cockroach injection test are as follows for percent mortality where differences were noted in favor of the polyurea meso-formulation. Differences between the formulations tested were noted at the 0.01% rate.

At the 0.01% concentration of indoxacarb at 2-7 days post-treatment, the polyurea mesocapsule formulation treatment increased the amount of German cockroach mortality by 20-30% as compared to the water based suspension concentration formulation treatment. This increased mortality indicates that indoxacarb in the polyurea mesocapsule formulation had greater efficacy at the 0.01% rate compared to the suspension concentrate formulation of indoxacarb.

The mortality expression of the formulations was tested when water based dilutions of the formulations were directly applied to German cockroaches in a topical bioassay. For the topical test, 10 adult male German cockroaches per treatment received 1 ul of each treatment topically applied to the pronotum via syringe. Cockroaches were anesthetized with $CO_2$ before and after treatment. Formulations were tested in Milli-Q-purified water dilutions yielding indoxacarb concentrations of 0.001%, 0.01%, 0.1% and 1%. The treated cockroaches were held in 60×15 mm petri dishes (one per dish) containing food and water in a laboratory controlled environment chamber. The treated cockroaches were checked daily for 7 days and the number dead were recorded. Food and water was refreshed as needed.

Referring now to FIG. 13, the results of the German cockroach topical test are as follows for percent mortality where differences were noted in favor of the polyurea meso-formulation. Differences between the formulations tested were noted at the 0.1% rate only.

At the 0.1% rate at 1-7 days post-treatment, the polyurea mesocapsule formulation treatment increased the amount of German cockroach mortality by 20-40% as compared to the water based suspension concentrate formulation treatment. This increased mortality indicates the indoxacarb polyurea mesocapsule formulation was able to enhance toxic activity at the 0.1% rate over the water based suspension concentrate formulation of indoxacarb. In addition, the polyurea mesocapsule formulation treatment also increased the speed of mortality as compared to the water based suspension concentrate formulation treatment of indoxacarb.

The ingestion bioassay was used to test mortality expression of the formulations when water based dilutions were ingested by German cockroaches. For the ingestion test, 10 adult male German cockroaches per 5 reps were placed into 100×25 mm petri dishes with a small cardboard harborage and a piece of Purina™ dog chow for food. Cockroaches were deprived of water for 3 days prior to exposure to the water based treated bait. Exposure to the water based treated bait was a no choice exposure for 30 minutes on days 1-3 where on day one 200 ul of bait was provided and on days two and three 150 ul of bait was provided. The water bait provided on day one was removed and replaced with new water bait on days 2 and 3. After the 3 days exposure to the water bait, the cockroaches were provided untreated water and food for the next 11 days. Formulations were diluted indeionized yielding indoxacarb concentrations of 0.0001%, 0.001%, 0.01%, and 0.1%. The treated cockroaches were checked daily for 15 days and the number dead were recorded. Quantity of water bait consumed was recorded for the 3 days this exposure occurred.

There were no differences between the formulations tested for percent mortality where the polyurea meso-formulation outperformed the water based suspension concentration formulation treatment of indoxacarb. However, at the 0.1% rate there were differences noted for bait consumption data. Referring now to FIG. 14, the results of the German cockroach ingestion test are as follows for mg consumption at the 0.1% rate.

At the 0.1% rate at 1 day post-treatment, the polyurea mesocapsule formulation bait treatment decreased the amount of bait consumption by German cockroaches by 86 mg as compared to the water based suspension concentration formulation bait treatment. This decreased consumption of the indoxacarb bait at the 0.1% concentration of indoxacarb in the polyurea mesocapsule formulation indicates quicker feeding reduction/cessation at day 1 compared to the water based suspension concentration formulation of indoxacarb.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A composition for the delivery of an agricultural active ingredient, comprising:
   a water phase; and
   a core-shell mesocapsule, the mesocapsule having a polymer shell surrounding a core within the polymer shell, the polymer shell having a hydrophilic outer surface at least partially in contact with the water phase, wherein the polymer shell is comprised of polyurea; and wherein at least a portion of the poorly water soluble agriculturally active ingredient is included in an oil phase in the core, the mesocapsule having a volume-average particle diameter between about 30 nm and about 500 nm and wherein the oil phase comprises about 1 wt. % to about 60 wt. % of the total weight of the composition wherein the polymer shell is further comprised of a compound having a first functional moiety and a second functional moiety, wherein the first functional moiety is selected from a primary amine, a secondary amine, a primary amino group, and a secondary amino group, and the second functional moiety is selected from the group consisting of carboxylate and trimethylamine.

2. The composition according to claim 1, wherein the polyurea is a reaction product of at least one polyisocyanate and at least one polyamine.

3. The composition according to claim 1, wherein the mesocapsule has a volume average diameter in the range of about 50 nm to about 300 nm.

4. The composition according to claim 1, wherein the shell includes hydrophilic functional groups and at least some of the hydrophilic functional groups contact water.

5. The composition according to claim 4, wherein the hydrophilic functional group on the surface of the shell is a carboxylate.

6. The composition according to claim 1 wherein the active ingredient has solubility in water of about 1,000 parts per million or less.

7. The composition according to claim 1, wherein the agriculturally active ingredient is selected from the group consisting of a herbicide, an insecticide, and a fungicide.

8. The composition according to claim 1, wherein the agriculturally active ingredient is selected from the group consisting of fenbuconazole, (3 S,6S,7R,8R)-8-benzyl-3-(3-(isobutyryloxymethoxy)-4-methoxypicolinamido)-6-methyl-4,9-dioxo-1,5-dioxonan-7-yl isobutyrate, epoxiconazole, atrazine, fluoroxypry-meptyl, spinosad, and indoxacarb.

9. The composition according to claim 1, wherein the composition comprises essentially no surfactant.

10. The composition according to claim 1, wherein the composition comprises less than 1 wt. % surfactant based on the weight of the oil phase.

11. The composition according to claim 1, wherein the composition comprises less than 0.5 wt. % surfactant based on the weight of the oil phase.

12. The composition according to claim 1, wherein the composition comprises no surfactant.

13. The composition according to claim 1, wherein the compound is selected from glycine, a salt of glycine, or a mixture of glycine and a salt of glycine.

14. The composition according to claim 1, wherein the agriculturally active ingredient comprises about 1.19 wt. % to about 5.73 wt. % of the total weight of the composition.

15. A composition for the delivery of an agricultural active ingredient, comprising:
a water phase;
a core-shell mesocapsule, the mesocapsule having a polymer shell comprised of polyurea and a compound having a first functional moiety and a second functional moiety, wherein the first functional moiety is selected from the group consisting of a primary amine, mine a primary amino group, and a secondary amino group, and the second functional moiety is selected from the group consisting of carboxylate and trimethylamine, the mesocapsule having a hydrophilic outer surface at least partially in contact with the water phase;
an oil phase comprising a poorly water soluble agricultural active ingredient, wherein at least a portion of the poorly water soluble agriculturally active ingredient is included in a core within the polymer shell, the mesocapsule having a volume-average particle diameter between about 30 nm and about 500 nm.

16. The composition according to claim 15, wherein the compound is selected from glycine, a salt of glycine, or a mixture of glycine and a salt of glycine.

17. The composition according to claim 15, wherein the composition comprises essentially no surfactant.

18. The composition according to claim 15, wherein the composition comprises less than 1 wt. % surfactant based on the weight of the oil phase.

19. The composition according to claim 15, wherein the composition comprises less than 0.5 wt. % surfactant based on the weight of the oil phase.

20. The composition according to claim 15, wherein the composition comprises no surfactant.

21. The composition according to claim 15, wherein the oil phase further includes between about 1 wt. % to about 90 wt. % of an organic solvent having a water solubility of about 10 g/100 ml or less.

22. The composition according to claim 15, wherein the oil phase further includes between about 0.5 wt. % to about 10 wt. % of an ultrahydrophobe.

23. A method of controlling insects, mites, plant diseases or weeds including the steps of:
providing a formulation including the composition of claim 1, and
applying an agriculturally effective amount of the formulation to at least one of the following: the plant, plant foliage, blossoms, stems, fruits, the area adjacent to the plant, soil, seeds, germinating seeds, roots, liquid and solid growth media, hydroponic growth solutions, treated surfaces, and into and onto the pest itself.

24. A method of controlling insects, plants diseases or weeds including the steps of:
providing a formulation including the composition of claim 1, and
applying an agriculturally effective amount of the formulation in mixture with one or more conventional formulations of agricultural active ingredients or nutrients to at least one of the following: the plant, plant foliage, blossoms, stems, fruits, the area adjacent to the plant, soil, seeds, germinating seeds, roots, liquid and solid growth media, hydroponic growth solutions, treated surfaces, and into and onto the pest itself.

* * * * *